United States Patent [19]

Conger, Sr.

[11] Patent Number: 4,648,840

[45] Date of Patent: Mar. 10, 1987

[54] DENTAL POLISHER COMBINING PRESSURIZED FLUID AND ABRASIVE FLOW

[76] Inventor: Stephen W. Conger, Sr., 10544 Sonata Dr., St. Louis, Mo. 63123

[21] Appl. No.: 765,813

[22] Filed: Aug. 15, 1985

[51] Int. Cl.⁴ .............................................. A61C 1/14
[52] U.S. Cl. .................................................... 433/125
[58] Field of Search .................. 433/125, 216; 51/321

[56] References Cited

U.S. PATENT DOCUMENTS 4,012,842  3/1977  Vit ........................................ 433/216
4,412,402  11/1983 Gallant ................................ 433/216

Primary Examiner—Robert Peshock
Attorney, Agent, or Firm—Paul M. Denk

[57] ABSTRACT

A dental polisher combining pressurized fluid and an abrasive flow for application to the teeth of a patient during performance of the cleaning function, the polisher incorporating a body means, having a pair of conduits therethrough, one conduit for providing flow of an abrasive material, the second conduit, being concentrically arranged, providing for flow of fluid, a supply housing provided rearwardly of the polisher body, incorporating a reservoir for holding a supply of abrasive material, the supply housing having an attachment area for connection of the standard dental equipment supply fitting that furnishes the air and water to dental instruments, and a delivery nozzle having a series of discharge ports therethrough connecting to the front of the polisher body, for discharging of the abrasive materials centrally of the nozzle, and a series of peripherally arranged and inwardly and laterally directed flows of fluid for combining with the discharged abrasive material.

11 Claims, 4 Drawing Figures

U.S. Patent   Mar. 10, 1987   4,648,840
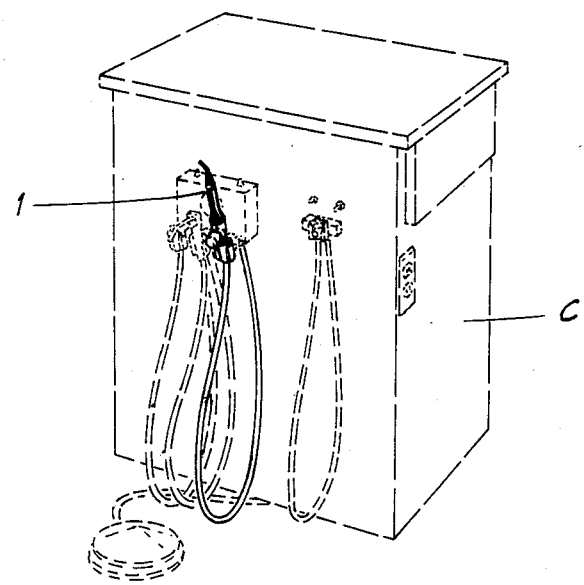
Fig. 1
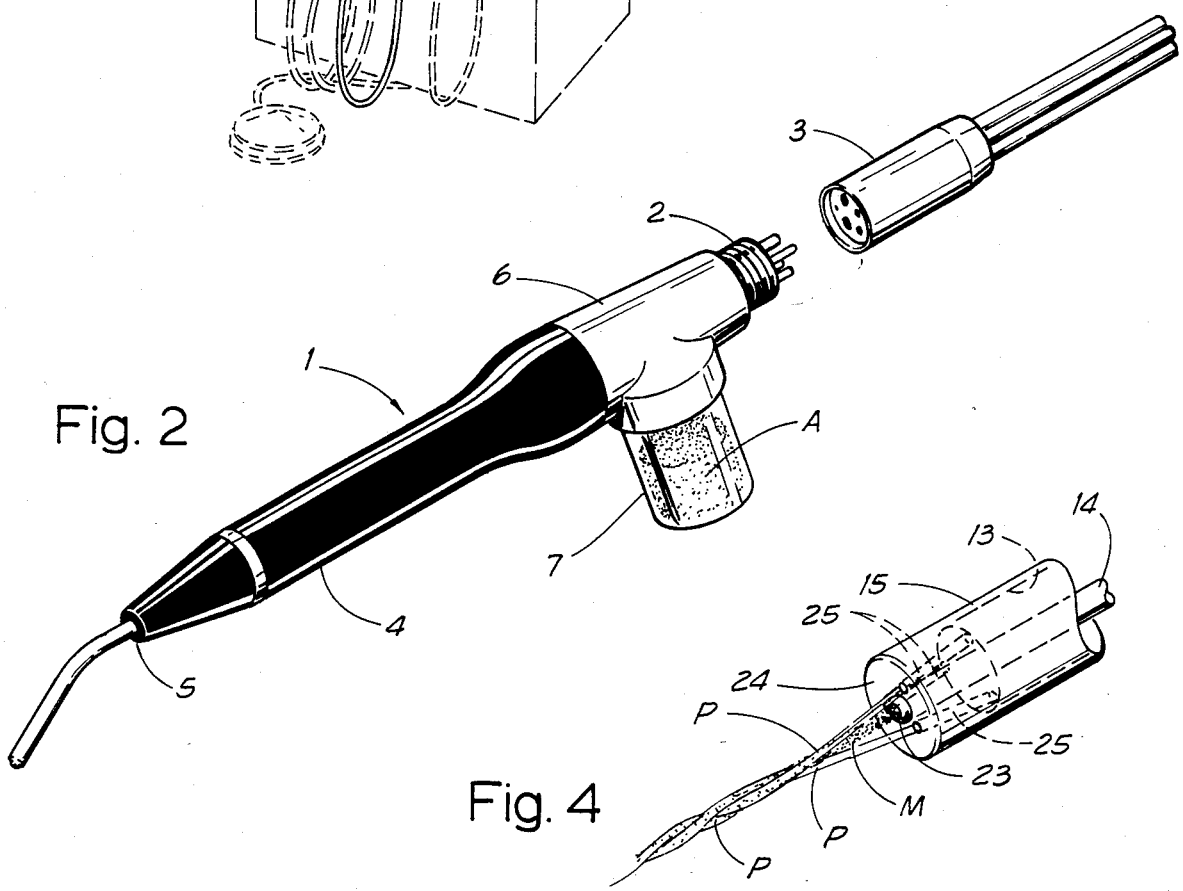
Fig. 2
Fig. 4
Fig. 3
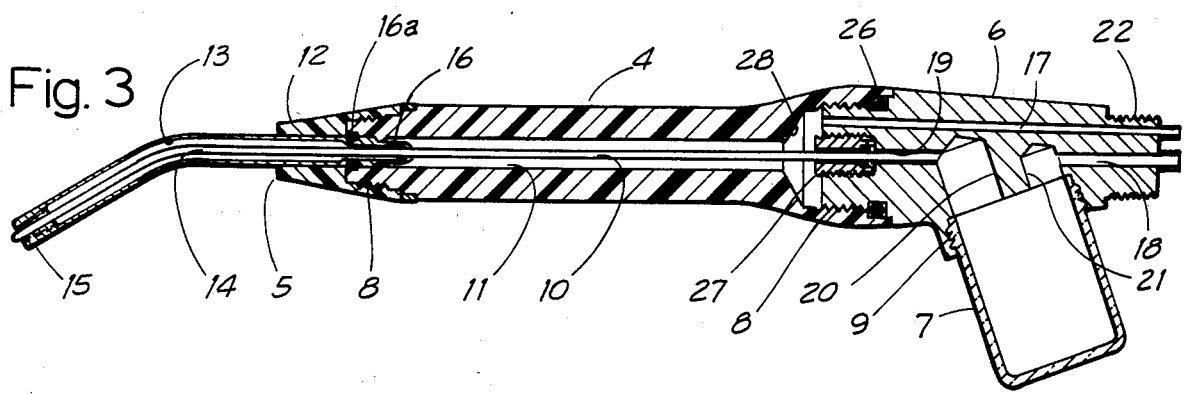

DENTAL POLISHER COMBINING PRESSURIZED FLUID AND ABRASIVE FLOW

BACKGROUND OF THE INVENTION

The subject matter of this invention relates generally to a dental polishing apparatus, of the type that incorporates the conveyance under pressure of a fluid, having an abrasive material entrained or confined therein, and for forceful application against the teeth of a patient to perform a polishing or cleaning function.

There are a large variety of prior developments relating to apparatuses that are useful in the dental profession for the treatment of patient's teeth, and generally, most of these apparatuses include various types of polishers, water delivery systems, pressurized air projectors, in addition to electrical drill means, and other appliances that are attached to a console that supplies them with the necessary electrical energy, air pressure, water pressure, and other discrete energies needed for application and usage of these type of devices. Instruments of these type are shown in the U.S. patent to Balamuth, No. 3,075,288, showing a dental instrument, in addition to another patent to the same and additional inventors, U.S. Pat. No. 3,212,537, pertaining to a supply and control apparatus for a vibratory cutting device. Another method for cleaning teeth, and the apparatus used in conjunction therewith, is shown in the U.S. patent to Gallant, No. 4,174,571. An additional patent to the same inventor upon equipment and method for delivering an abrasive-laden gas stream is shown in the U.S. Pat. No. 4,412,402. A related type of air-abrasive prophylaxis equipment is shown in the U.S. patent to Black, No. 3,882,638. Another patent showing the use of an abrasive for application for removing a coating is shown in the McFaddan patent No. 2,876,601. The Caron U.S. Pat. No. 3,163,963, shows a blaster device, wherein the abrasive material is held within its cannister associated with the instrument. A multi-purpose dental syringe apparatus is shown in the patent to Jones, U.S. Pat. No. 3,593,423. Another device for cleaning teeth is shown in the Landgraf U.S. Pat. No. 4,462,803. A further type of device for surface treatment of teeth is shown in the Hain, et al U.S. Pat. No. 4,482,322. Another dental cleaning system is shown in the patent to Warren, U.S. Pat. No. 4,487,582. And, a sand blasting apparatus wherein a supply of polishing material is provided within a reservoir connecting with its air tube for delivery of abrasive material to the situs of cleaning is shown in the U.S. Pat. No. 3,793,778.

In most instances, where a teeth polishing apparatus is employed, generally it is marketed in combination with its own operational unit, which not only supplies the delivery of power, water, and abrasive material to the hand held instrument, for attaining a polishing of teeth, but the overall assembly is marketed as a rather expensive integral unit for achieving just that singular result, and that is to provide polishing of the teeth. Numerous of these types of units are available upon the market, and in every instance the polishing instrument is associated with its own particular operational console that furnishes its necessary ingredients for attaining overall operation of the polishing instrument.

SUMMARY OF THE INVENTION

This invention relates generally to a dental appliance, and more specifically pertains to a dental polisher that incorporates all of the necessary ingredients for attaining abrasive polishing of the patient's teeth, and which can be attached directly to the standard operational console available in every dental office.

This invention contemplates the formation of a hand held apparatus that may be easily grasped by the dentist, contains a reservoired supply of abrasive material such as plain bicarbonate of soda, or a mixture of bicarbonate of soda and salt, or other types of compositions that are utilized by the dentist for the cleaning and polishing of teeth. The invention incorporates a body portion that has sufficient length to provide for its convenient grasping by the dentist during usage, and has a delivery nozzle provided at its forward end, generally threadedly engaged thereon, that uniquely delivers select streams of the abrasive composition, generally conveyed under the influence of pressurized air, releasing the same generally centrally of the formed nozzle, while at the same time separately discharging a series of jets of pressurized fluid, such as water, surrounding the released abrasive, in order to properly entrain and convey the abrasive within a selected pattern at the surface of the teeth, and preventing the discharge of dust, or other remnants of powder that would ordinarily cause a problem proximate to the patient's mouth, adding to his/her discomfort. In addition, and in order for this invention to provide a localized delivery of the abrasive to a particular situs at the surface of the patient's teeth, the discharged jets of fluid are arranged not only concentrically around the surface of the conveyed abrasive, but are likewise inclined slightly inwardly, at a particular range of degree, in addition to being somewhat laterally directed, in order to move the streams of pressurized fluid, generally three in number, into a helical or spirally arranged flow pattern at the periphery of the discharging abrasive. Hence, the combination of the centrally discharged abrasive, and the surrounding discharged jets of fluid, converge into a combination jet that provides for a focal impingement of the abrasive against the surface of the teeth for assuring more efficient and effective cleaning.

In addition to the foregoing, that discharge port for the abrasive composition is located slightly forwardly of the discharges for the streams of fluid, so that the likelihood that the abrasive powder will become compacted at the location of its dishcarge is minimized, assuring the dentist that the instrument will be ready for usage, problem free, each time it is employed for usage. There has been a problem with prior type teeth polishing apparautses where the abrasive composition when discharged at the same surface or inwardly from where the water jets are projected becomes rather compacted and clogged at that location, requiring that the instrument must be recleaned, particularly at its discharge nozzle end, before each application. This particular problem is minimized, if not eliminated, through the usage of the fabricated structure for the tooth polisher as identified in this disclosure.

The body means for this polisher has connected at its back end a supply housing means, through which individual delivery of pressurized fluid is conveyed, separate from the conveyance of pressurized air into the housing, where the latter picks up the abrasive composition from an appended reservoir, and further conveys it through the housing, the body means of the apparatus, for delivery and discharge from the identified nozzle, in the manner as previously described. The supply housing includes a series of cavities, there being two in number, with which the flow lines for the pressurized air is conveyed, with each cavity communicating with the interior of the abrasive reservoir ladened, to assure that as the pressurized air is conducted into the reservoir, it picks up a determined quantity of abrasive, and conveys it further along the apparatus for its discharge during application of the polishing instrument of this invention.

What is unique about this particular development is that the entire instrument, which is integrated into a single apparatus, can connect directly with the standard two, three, four or multi hole connector or fitting that generally accompanies any dental instrument package readily available within the dental office. Such a fitting not only includes a series of lines for conveying of air under pressure, in addition to fluid or water under pressure, but likewise furnishes means for achieving exhaust. Such a connector or fitting is readily available in the art, such as from Healthco Dental Supply, of St. Louis, Mo. These types of fittings are frequently used upon the standard dental instrument console, readily available in the art.

This particular device is designed to become an extremely handly and low-cost hand piece type of polishing apparatus which is completely self contained, being so engineered that it can attach directly with the connector, adapter, or fitting readily available with any dentist console unit, generally known as the delivery system for the dental office. This tool is easily cleaned, and in fact is rather self cleaning, since it incorporates a type of nozzle that prevents the caking of the powder or abrasive composition during or after its application. The tool is designed so that it can be easily handled by the dentist, for single handled usage, freeing the dentist's other hand for holding of the mirror, or other instrument, utilized during a polishing function.

These and other objects of this particular development will become more apparent to those skilled in the art upon reviewing the description of the preferred embodiment in view of the drawings provided herein.

BRIEF DESCRIPTION OF THE DRAWING

In referring to the drawing,

FIG. 1 discloses the polishing apparatus of this invention, attaching to the standard dental tubing and supply console unit readily available in the art, as disclosed in phantom line;

FIG. 2 is an isometric view of the polishing apparatus of this invention, shown in the process of connecting with the standard dental fitting of a console unit;

FIG. 3 is a longitudinal sectional view taken along the length of the dental polisher of this invention; and FIG. 4 discloses the delivery nozzle for the polisher of this invention, projecting the polishing composition.

DESCRIPTION OF THE PREFERRED EMBODIMENT

In referring to the drawing, and more particularly FIG. 2, the dental polisher 1 of this invention is clearly disclosed, and showing, as at its back and, having a connector 2 readily disposed for attachment with the standard fitting 3 readily available at any dental console, as at C disclosed in FIG. 1. As can be seen in FIG. 1, the dental polisher of this invention 1 is shown as an add-on instrument that can be readily connected with the standard dental unit as frequently available in any dentist's office. Generally these units provide a series of tubing that conveys combinations of pressurized air, fluid such as water, exhaust lines, or the like, from the consoles C and to the dental appliance, whether it be a drill, water delivery instrument, air instrument, and the like.

The polisher 1 of this invention is formed having a body portion 4 incorporating a nozzle means 5 at its forward end, and from which the various polishing ingredients comprising the combination of a fluid such as water and the abrasive material are discharged, under pressure, while at the back end of the polisher there is located the supply housing means 6 and generally through which the fluid under pressure is conveyed, in addition to pressurized air passing therethrough and which picks up a quantity of the abrasive material, such as disclosed at A, contained within the reservoir or cannister 7.

A more detailed disclosure of the polisher is shown in FIG. 3. As can be seen, the combination of the body means 4, the nozzle 5 and the supply housing 6 are secured together into an integral unit, generally held together by means of the threaded connections, as shown at 8. In addition, the reservoir 7 conveniently connects to its housing 6, through any form of connection, such as the threaded connection 9, as can be seen.

The body 4 has a series of passages provided therethrough, such as an internal tubing forming the conduit 10 and through which the abrasive material, such as previously defined, is conveyed. In addition, there is a concentrically arranged passage or conduit 11 around the previously identified conduit 10. These particular conduits extend further into the nozzle means 5, and as can be seen, the nozzle incorporates the connecting member or end cap 12 and which has the forwardly extending nozzle formed of the tube 13, concentrically arranged around the internal conduit 14. The internal conduit 14, which is an extension of the conduit 10, conveys the abrasive material, under the force of the passing pressurized air, while the conduit 13, which commensurates with the passage or conduit 11, conveys the fluid to the tip 15 of the nozzle structure. At the connection between the end cap 12 and the body means 4, as can be seen, there is provided an O-ring 16 a useful for sealing the upper end of the conduit 13, with the forward end of the body 4 of the instrument. But, there is still sufficient clearance provided between the conduit 13, and its internally arranged conduit 14, such as at 16, to assure adequate space for the continuing flow of the fluid under pressure through the instrument, during usage.

The supply housing 6 likewise threadily engages, as at 8, with the back end of the polisher body 4. As can be seen, a conduit 17 is provided through the housing 6, and conveys a supply of fluid, from the fitting 3, and its console C, to the housing 4, emptying into the chamber 28 integrally formed therein. In addition, there is another conduit formed through the housing 6, disclosed as a pair of flow lines 18 and 19, with each of these flow lines communicating with a respective cavity, as at 20 and 21, formed within the said supply housing. These cavities are opened into the reservoir 7, for pickup of a quantity of the abrasive material contained therein, as the pressurized air flows through the lines 18 and 19, through the conduits 10 and 14, for discharge out of the nozzle tip or port 15.

Also, it is to be noted that the back end of the supply housing 6 incorporates a threaded or otherwise fitting 22, and upon which the connector 3 attaches for alignment with and providing communication to the instrument of the various discrete supplies of air, fluid, exhaust line, and the like, that furnish the operating characteristics to the dental polisher of this invention.

The particular style of nozzle incorporated into the structure of this polisher is shown in FIG. 4. This nozzle, disclosed at 15, has the conduit 14 extending therethrough, and which conduit, at its forwardmost tip 23, projects slightly forwardly of the frontal facing 24 of the shown nozzle. In addition, the conduit 13 separates into a series of discrete flow paths or ports 25, there being three in number as shown, and these nozzles are provided for furnishing directional discharge of the fluid from the nozzle during application of the polisher. For example, these flow paths are angled slightly towards the center, by one or more degrees, and in addition, are angulated slightly laterally, by a minimum of degrees, in order to afford a rather peripheral and swirling arranged pattern for the combination of fluid and its abrasive composition being discharged from the nozzle tip. As can be seen, the abrasive material M discharges centrally from the conduit 14, while the discrete flow paths P of the fluid discharge surrounding the same, and converge into a composite polishing composition some distance forwardly of the nozzle facing 24, or the abrasive material discharge tip 23. The prime benefit to be achieved from this arrangement is that there is a focal point forwardly of the nozzle tip that provides for a commingling of these ingredients at that particular point and which provides the most effective cleaning of the tooth if the instrument is held that particular dimension from the tooth surface, during a cleaning function. In addition, having the abrasive material's tip slightly forwardly of the fluid's discharge ports, as at the facing 24 of the nozzle, once the instrument is shut off, the abrasive powder at the surface of the tip is yet dry, and does not become compacted or congealed at this location, which in the standard and currently available type of tooth polishing instrument, not only must be cleaned after each usage, or before any reapplication.

In order to insure that a fluid tight seal is provided throughout the length of the instrument, where the end cap threadily engages onto the body means 4 of the instrument, as previously explained, an O-ring 16 is provided thereat in order to afford an adequate seal. In addition, where the supply housing 6 threadily engages within the body means 4, adequate seals are likewise provided at that location, such as through the provision of an O-ring 26 to present a fluidic seal thereat. In addition, another fitting 27 is threadily engaged within the front of the supply house 6, in order to assure proper alignment and holding of the conduit 10, and the flow line 19, together. It is also to be noted that the entire arrangement of the flow lines 18 and 19, the conduits 10 and 14, are all axially aligned centrally of the entire instrument, so that as the threaded connections are made between the various polisher components, as previously defined, the abrasive material's flow lines or conduits will be conveniently aligned for proper operation, without leakage, throughout the length of the instrument. In addition, the fluid flow lines and conduits are likewise conveniently and generally concentrically arranged to assure their proper functionings, and to prevent any intermixing of the fluids or abrasive material within the instrument, and not until they converge some distance forwardly of the nozzle as previously explained.

Variations or modifications to the structure of this invention may occur to those skilled in the art upon reviewing the subject matter of this disclosure. Such variations or modifications, if within the spirit of this invention, are intended to be encompassed within the scope of any claims to patent protection issuing hereon. The description of the preferred embodiment set forth herein, and as shown in the drawing, is provided for illustrative purposes only.

Having thus described the invention what is claimed and desired to be secured by Letters Patent is:

1. A dental polisher combining pressurized fluid and an abrasive flow for application to the teeth of a patient during performance of a cleaning function, said polisher capable of attaching with a standard supply fitting, comprising, a body means having a length to be conveniently grasped and held by the hand during application of the polisher, said body means having a pair of conduits therethrough, one conduit being a fluid conveying conduit, and the other being an abrasive conveying conduit, a delivery nozzle provided forwardly of the body means, connecting therewith, and useful during application for separately discharging the fluid and abrasive while providing for their convergence forwardly of the nozzle and into a combined flow, a supply housing means provided rearwardly of the body means and incorporating a pair of additional conduits for accommodating separate flows of the fluid and abrasive and each communicating with the respective conduits provided through the body means, a reservoir connecting with the housing means and provided for holding a supply of abrasive, the said abrasive conduit through the housing means formed into two flow lines, one of said flow lines at one end communicating with the interior of the reservoir, and at its other end opening for attaching with the supply fitting, the other flow line at one end also communicating with the interior of the reservoir and at its other end opening for communication with the abrasive conveying conduit provided through the body means, wherein air under pressure traversing said abrasive conduits entraining said reservoired abrasive for conduct through and discharge from the said delivery nozzle, said delivery nozzle having a series of discharge ports therethrough, one of said discharge ports being centrally disposed and communicating with the abrasive conveying conduits and provided for releasing a stream of the pressurized air entrained abrasive, and a series of additional fluid discharge ports surrounding said central port, and communicating with the fluid conveying conduits and providing for release of a series of streams of fluid substantially surrounding the discharged abrasive stream, and wherein said abrasive discharge port of the nozzle extending further forwardly than the fluid discharge ports of the same nozzle.

2. The invention of claim 1 and wherein said fluid discharging ports being angled inwardly and laterally to produce helically flowing streams of fluid for peripherally combining with the discharged abrasive.

3. The invention of claim 1 and wherein said fluid conveying conduit being concentrically arranged around the abrasive conveying conduit provided within the body means.

4. The invention of claim 3 and wherein said abrasive conveying conduit and concentrically arranged fluid conveying conduit partially extending through said discharge nozzle.

5. The invention of claim 4 and including a series of additional fluid conveying conduits communicating with said concentric fluid conveying conduit and opening at a series of discharge ports for delivery of the pressurized fluid into peripherial flowing streams of fluid for tangentially combining with the discharged abrasive.

6. The invention of claim 3 and there being a fluid chamber provided at the back end of the body means for delivery of fluid to the fluid conveying conduit formed within the said body means.

7. The invention of claim 1 and including said supply housing means having a pair of cavities formed therein, said cavities communicating with the reservoir, and one of said flow lines communicating with one of each cavity.

8. The invention of claim 1 and wherein said delivery nozzle and supply housing means being threadedly engaged with the body means.

9. The invention of claim 1 and wherein said reservoir being threadedly engaged with the supply housing means.

10. The invention of claim 9 and wherein said reservoir extending downwardly from the supply housing means.

11. The invention of claim 1 and wherein said abrasive conveying conduits and being axially aligned through the nozzle, body means, and supply housing means.

* * * * *